(12) United States Patent
Stegmann et al.

(10) Patent No.: US 6,726,676 B2
(45) Date of Patent: Apr. 27, 2004

(54) METHOD OF AND DEVICE FOR IMPROVING THE FLOW OF AQUEOUS HUMOR WITHIN THE EYE

(75) Inventors: Robert Stegmann, Pretoria (ZA); Hans R. Grieshaber, Schaffhausen (CH)

(73) Assignee: Grieshaber & Co. AG Schaffhausen, Schaffhausen (CH)

( * ) Notice: Subject to any disclaimer, the term of this patent is extended or adjusted under 35 U.S.C. 154(b) by 0 days.

(21) Appl. No.: 09/478,047

(22) Filed: Jan. 5, 2000

(65) Prior Publication Data

US 2003/0139729 A1 Jul. 24, 2003

(51) Int. Cl.$^7$ .............................................. A61M 25/00
(52) U.S. Cl. ...................... 604/523; 604/533; 604/187; 604/239
(58) Field of Search ................... 604/48, 521, 93.01, 604/181, 187, 264, 239, 523, 533–535; 623/23.64

(56) References Cited

U.S. PATENT DOCUMENTS

| | | | |
|---|---|---|---|
| 3,949,750 A | | 4/1976 | Freeman |
| 4,936,825 A | | 6/1990 | Ungerleider |
| 5,360,399 A | * | 11/1994 | Stegmann .................... 604/28 |
| 5,486,165 A | | 1/1996 | Stegmann |
| 5,626,558 A | | 5/1997 | Suson |
| 6,162,202 A | * | 12/2000 | Sicurelli et al. ............ 604/272 |

FOREIGN PATENT DOCUMENTS

| | | |
|---|---|---|
| EP | 0 898 947 A | 3/1999 |
| WO | WO 95 08310 A | 3/1995 |

* cited by examiner

Primary Examiner—Brian L. Casler
Assistant Examiner—Catherine S. Williams
(74) Attorney, Agent, or Firm—Henry M. Feiereisen; Ursula B. Day

(57) ABSTRACT

A method for improving the draining of aqueous humor in an eye of a living being and a device for widening the Schlemm's canal is described wherein a first incision is made in a lamellar section of the sclera to form a first scleral flap which is then folded upwards in the direction of the cornea, thereby creating a recess in the sclera. A second scleral flap is formed by incising a second lamellar section in the area of the recess and lifted upwardly in the direction of the first sclera flap, thereby exposing two opposite openings into the Schlemm's canal into which an expanding medium is injected into the Schlemm's canal; formation of a slitlike passageway connecting the aqueous humor-permeable with the subscleral space is realized by detaching the Descemet-membrane on the area of the Schwalbe's line by means of a slight pressure force; and subsequently, the first scleral flap folded back, after severance of the second scleral flap, for placement upon a support surface formed as a consequence of the incision of the second lamellar section. Subsequently, a viscous medium is injected into a subscleral space formed behind the first scleral flap and the first scleral flap is rejoined to the sclera.

13 Claims, 8 Drawing Sheets

FIG. 10
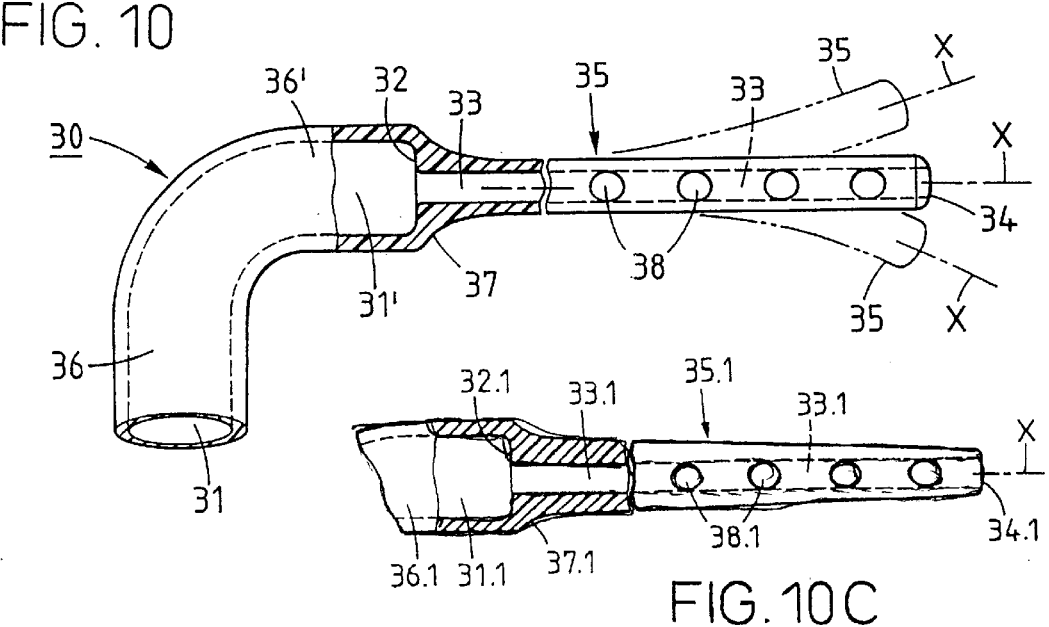
FIG. 10C
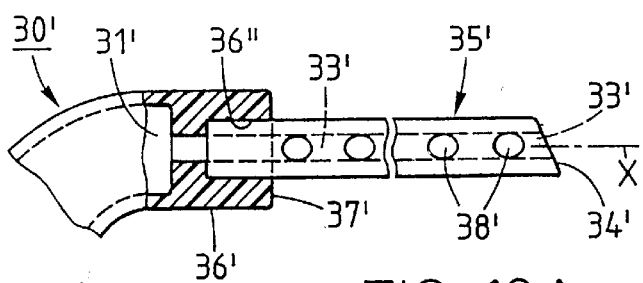
FIG. 10A
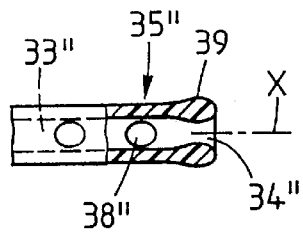
FIG. 10B
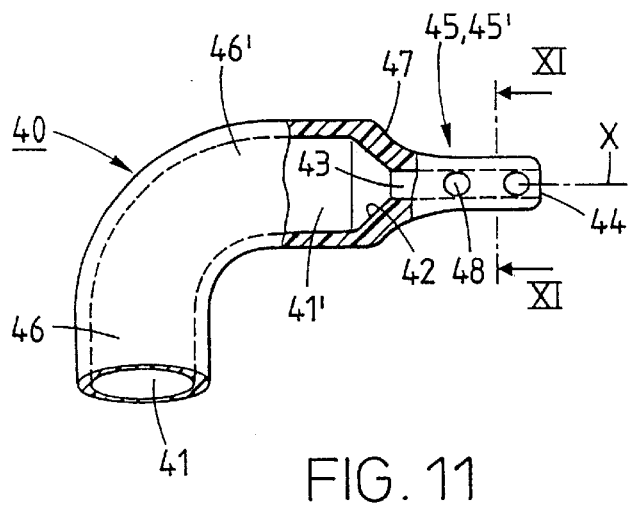
FIG. 11
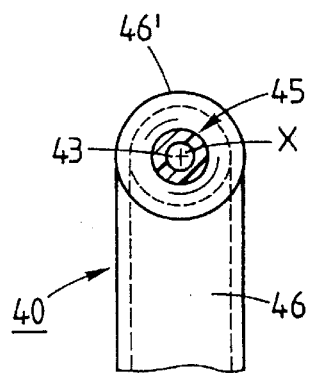
FIG. 11A

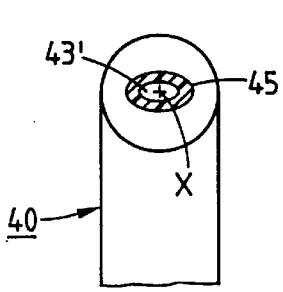 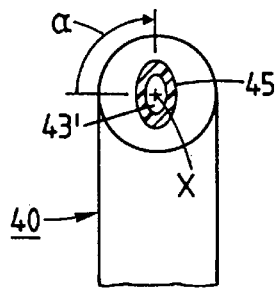 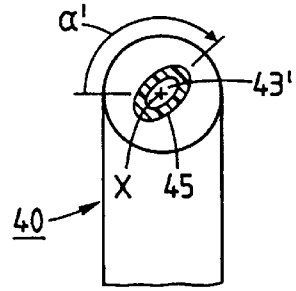
FIG. 11B    FIG. 11C    FIG. 11D
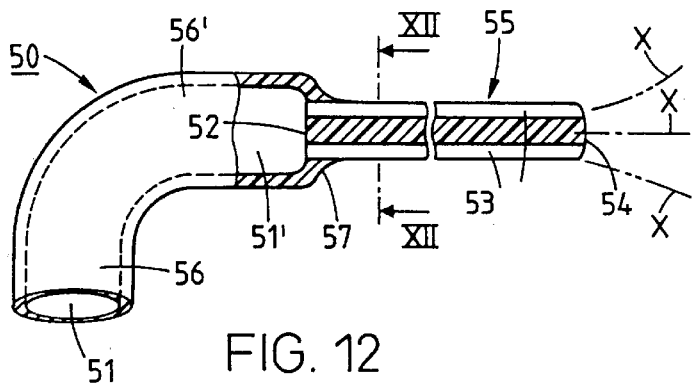 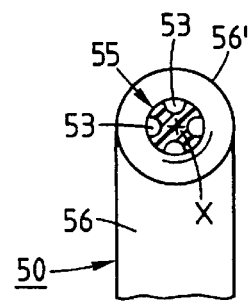
FIG. 12    FIG. 12A
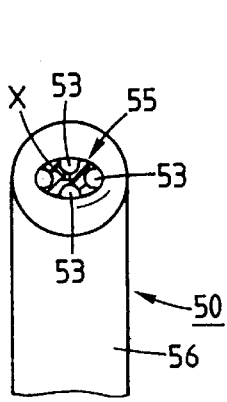 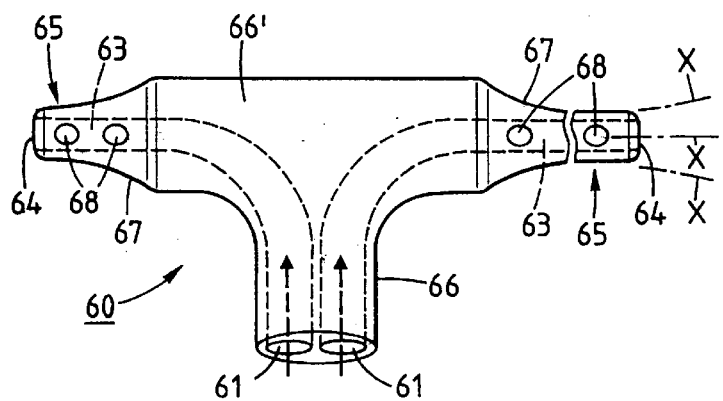
FIG. 12B    FIG. 13

METHOD OF AND DEVICE FOR IMPROVING THE FLOW OF AQUEOUS HUMOR WITHIN THE EYE

BACKGROUND OF THE INVENTION

The present invention relates, in general, to a method for improving a drainage of aqueous humor within the eye of a living being, and to a device for widening the circular canal of Schlemm to improve drainage of aqueous humor.

If the trabecular meshwork is either partially or completely non-functional due to an obstruction or back-up, or pathological changes, natural flow of the aqueous humor becomes limited, thereby raising the pressure inside the eye which negatively impacts on the blood circulation and the function of the visual nerve. The resulting disease is commonly known under the name "glaucoma" which may lead to blindness in the eye.

U.S. Pat. Nos. 5,360,399 and 5,486,165 describe a method and apparatus, by which the trabecular meshwork, which is located upstream of the canal of Schlemm and which due to pathological changes, may either partially or completely obstruct the outflow of aqueous humor, is essentially widened by the hydraulic pressure of a highly viscous aqueous solution, which when injected into the canal of Schlemm opens it at several location points, so that an outflow of the aqueous humor can be realized.

Surgical methods are known for increasing the flow of aqueous humor within the eye, in particular, when the outflow of the aqueous humor is diminished. However, surgical methods which open the canal of Schlemm and the trabecular meshwork have not necessarily led to the required success in the long term because, for example, regeneration of the tissue closes the openings in the trabecular meshworks.

SUMMARY OF THE INVENTION

It is thus an object of the present invention to provide an improved method for realizing an enhanced flow of aqueous humor within the eye, obviating the afore-stated drawbacks.

In particular, it is an object of the present invention to provide an improved method by which the necessary drainage of the aqueous humor via the outflow pathways of the eye is realized and which thereby results in an improved circulation of the aqueous humor in the eye and thus regulating the pressure within the eye.

These objects, and others which will become apparent hereinafter, are attained by a method in accordance with the present invention which includes the following steps: incising a first lamellar section of the sclera to form a first scleral flap; lifting the first scleral flap upwards in the direction of the cornea, thereby creating a recess in the sclera; incising a second lamellar section in the area of the recess to thereby form a second scleral flap and a support surface bounding the scleral flap; lifting the second scleral flap upwards in the direction of the first sclera flap, thereby exposing two opposite openings into the Schlemm's canal; injecting an expanding medium through the openings into the Schlemm's canal; folding the first scleral flap back, after severance of the second scleral flap, for placement upon the support surface, thereby confining a subscleral space adjacent the first scleral flap; injecting a viscous medium into the subscleral space; and rejoining the first scleral flap to the sclera.

In accordance with a further feature of the present invention, a slit-like passageway is formed between the subscleral space and the anterior chamber by applying a pressure force against a peripheral edge of the aqueous humor-permeable Descemet's membrane to detach the Descemet's membrane from the cornea. In this manner, the aqueous humor, which normally flows into the canal of Schlemm via the trabecular meshwork, flows additionally by way of Descemet's membrane from the anterior chamber in fluid connection therewith, and the slit-like passageway, into the subscleral chamber.

According to another feature of the present invention, severance of the second scleral flap can be executed at any time after lifting the second scleral flap and before folding back the first scleral flap, i.e. before or after injection of expanding medium into the canal of Schlemm or before or after detachment of the Descemet's membrane.

It is a further object of the present invention to provide an improved device for expanding a surgically exposed Schlemm's canal in an eye to thereby realize an enhanced flow of aqueous humor.

This object is attained in accordance with the present invention by providing a probe insertable into the Schlemm's canal for injecting a viscous medium to thereby generate a localized pressure buildup, with the probe having an outlet port which is defined by a diameter and an axial length, whereby the length is sized at least twice the diameter of the outlet port.

The probe is suitably connected to a pressure source for supply of expanding medium via an adapter and includes a tube which is connected to the adapter and has a circular ring shaped or elliptic cross section. The adapter may have an arcuate configuration, and the tube may have an inner axial bore which forms the outlet port and is in fluid communication with an interior space of the adapter for conduction of the expanding medium to the Schlemm's canal. Alternatively, the tube may have an outer periphery formed with an axial groove which forms the outlet port and is in fluid communication with an interior space of the adapter for conduction of the expanding medium to the Schlemm's canal.

According to another embodiment of the present invention, the adapter may have a T-shaped configuration and include a vertical portion and a horizontal portion formed integrally with the vertical portion for attachment of two of probes in opposite disposition, wherein each of the probes has an inner axial bore which forms part of the outlet port and is in fluid communication with an inlet port in the vertical portion of the adapter. The vertical portion is suitably connected to the pressure source via a feed conduit such that expanding medium is injected into the Schlemm's canal via the inner axial bore of both probes simultaneously or sequentially.

According to still another feature of the present invention, the probe has a distal end and a proximal end and includes a transition piece which is secured to the proximal end of the probe for attachment to the adapter, with the transition piece having a conical configuration or a circular arc shaped configuration.

The probe may be formed in one piece with the adapter, or the probe may be securely fixed in a complementary recess of the adapter. Suitably, the probe is made of flexible plastic material, e.g. transparent plastic, or may be made of a metal tube or, a flexible tube from metal, e.g. a nickel titanium alloy.

BRIEF DESCRIPTION OF THE DRAWING

The above and other objects, features and advantages of the present invention will now be described in more detail with reference to the accompanying drawing in which:

FIG. 10 is a partially sectional view, on an enlarged scale, of a first embodiment of a united adapter-probe arrangement according to the invention;

FIG. 10A is a partially sectional cutaway view of a variation of the adapter-probe arrangement of FIG. 10;

FIG. 10B is a partially sectional cutaway view of another variation of the adapter-probe arrangement of FIG. 10;

FIG. 10C is a partially sectional view on an enlarges scale, of a variation of a united adapter-probe arrangement according to the invention.

FIG. 11 is a partially sectional cutaway view of still another embodiment of a united adapter-probe arrangement according to the present invention;

FIG. 11A is a partially sectional view of the adapter-probe arrangement, taken along the line XI—XI in FIG. 11;

FIG. 11B is a partially sectional view of an adapter-probe arrangement, showing a first variation of the probe;

FIG. 11C is a partially sectional view of an adapter-probe arrangement, showing a second variation of the probe;

FIG. 11D is a partially sectional view of an adapter-probe arrangement, showing a third variation of the probe;

FIG. 12 is a partially sectional cutaway view of yet an other embodiment of a united adapter-probe arrangement according to the present invention;

FIG. 12A is a partially sectional view of the adapter-probe arrangement, taken along the line XII—XII in FIG. 12;

FIG. 12B is a partially sectional view of the adapter-probe arrangement of FIG. 12, showing a variation of the probe;

FIG. 13 is a schematic illustration of the T-shaped adapter of FIG. 6 with two probes in opposite disposition formed to the adapter.

DETAILED DESCRIPTION OF PREFERRED EMBODIMENTS

Figure 1:
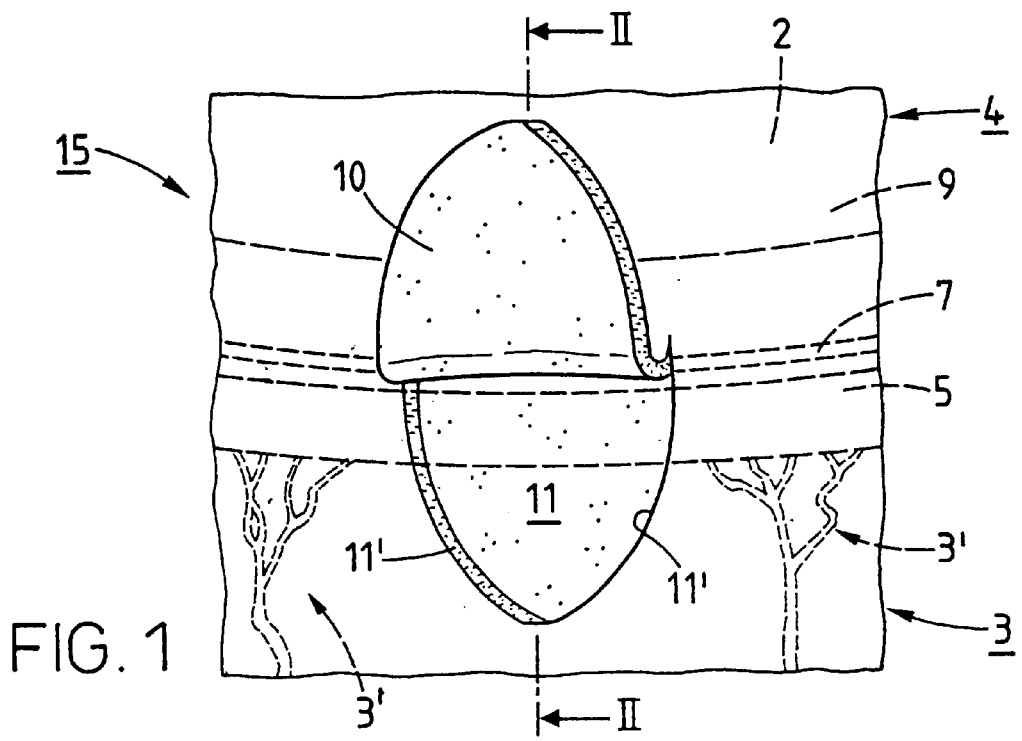
FIG. 1 is a schematic illustration of a portion of a eye, on an enlarged scale, showing a first parabolic incision in the sclera for forming a first scleral flap which is folded upwards.

Throughout all the Figures, same or corresponding elements are generally indicated by same reference numerals.

Turning now to the drawing, and in particular to FIG. 1, there is shown a first process step for improving a drainage of aqueous humor in an eye 15 which is shown only schematically by way of a portion of an iris 2, a cornea 4, a sclera 3, a partial section of the circular Schlemm's canal 5 (sinus venosus sclerae) and outflow pathways 3' which is comprised of a multitude of collector channels for conducting the aqueous humor. In the initial phase of the process according to the invention, a first incision of approximately parabolic shape is made in the sclera 3 to form a scleral flap 10 which is lifted upwards in the direction towards the cornea 4 to thereby expose a corresponding recess 11 which is bounded by a circumferentially extending side wall 11'. The scleral flap 10 is held in upwardly folded position by a tool or other means which are not shown for the sake of simplicity but are generally known by the artisan.

Figure 2:
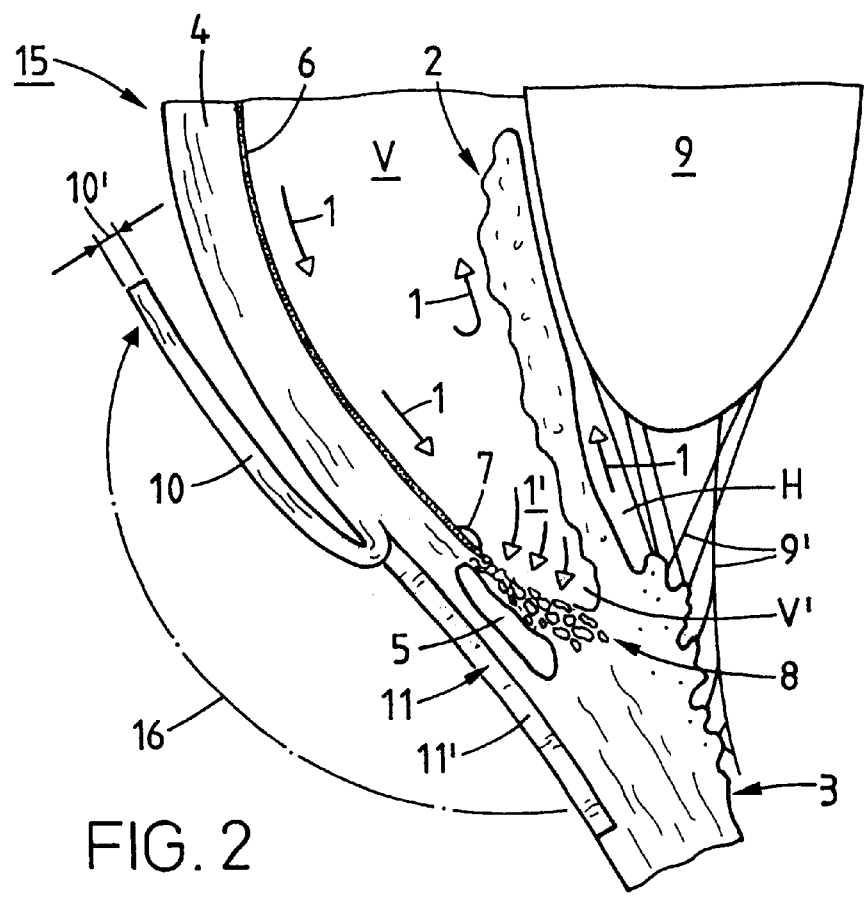
FIG. 2 is a schematic view of the portion of the eye of FIG. 1, taken along the line II—II in FIG. 1.

FIG. 2, which is a sectional view of the portion of the eye 15, taken along the line II—II in FIG. 1, shows a portion of the sclera 3, a portion of the cornea 4 with the Descemet membrane 6 and the Schwalbe's line 7, a portion of the iris 2 and a portion of the lens 9 connected to the sclera 3 by means of the zonular fibers 9'. Further shown is the first scleral flap 10 which has been lifted upwards in the direction of arrow 16 and the corresponding recess 11, in addition to the canal of Schlemm 5 with the trabecular meshwork 8 (trabecular meshwork) disposed anteriorly thereof.

Arrows 1 and 1' in FIG. 2 designate essentially the circulation of aqueous humor and the natural drainage thereof. The aqueous humor, which in a healthy eye, regenerates continually, flows according to arrow 1 from the posterior chamber H to the anterior chamber V and is conducted at the iridocorneal angle V' in the direction of arrow 1' via the trabecular meshwork 8 into the Schlemm's canal 5 and from there, via outflow pathways 3' (FIG. 1) into the natural venous system (not shown). When the trabecular meshwork 8 is partially or completely non-functional due to back-up or like blockage, the natural drainage of aqueous humor is limited to such an extent that the pressure inside the eye 15 rises to thereby restrict the blood circulation and thus the functionality of the optic nerve (not shown). The resulting disease is commonly known under the name "glaucoma" and may lead to blindness of the affected eye.

Before incising the sclera 3 in a manner shown in FIG. 1, a micro-surgical procedure is carried by which the conjunctiva (not shown) is retracted with a suitable tool for exposing a sufficient portion of the sclera 3. After the first incision, the formed scleral flap 10 is folded upwards in the direction towards the cornea 4, thereby exposing the first recess 11 with its circumferential side wall 11'. The first incision may cover an area of, for example, 3 mm×3 mm with a depth which is so selected that the thickness 10' of the first sclera flap 10 is approximately ⅓ of the natural thickness of the sclera 3 in this zone, as depicted in FIG. 2. In this first phase, the Schlemm's canal 5 is not yet exposed.

Figure 3:
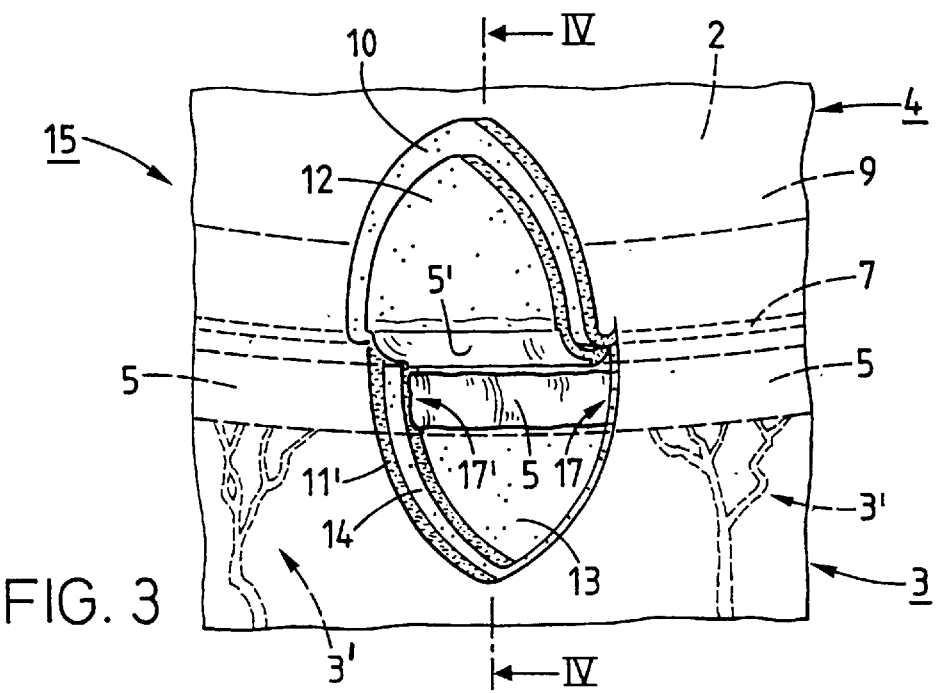
FIG. 3 is a schematic illustration of the portion of the eye of FIG. 1, showing a second parabolic incision within the area of first incision for formation of a second scleral flap which is folded upwards.

In the next process step, as shown in FIG. 3, a second incision is made within the area of the first incision to form a second parabolic scleral flap 12 which is then lifted upwards in the direction of the cornea 4, so that a second recess 13 is defined in correspondence with the second scleral flap 12 and bounded by a support surface 14. The depth of the second incision is selected such that the Schlemm's canal 5 is now exposed over the entire width of the second recess 13. In this phase, two openings 17 and 17' of the Schlemm's canal 5 in opposite disposition in the recess 13 are accessible for injection of an expanding medium.

Figure 4:
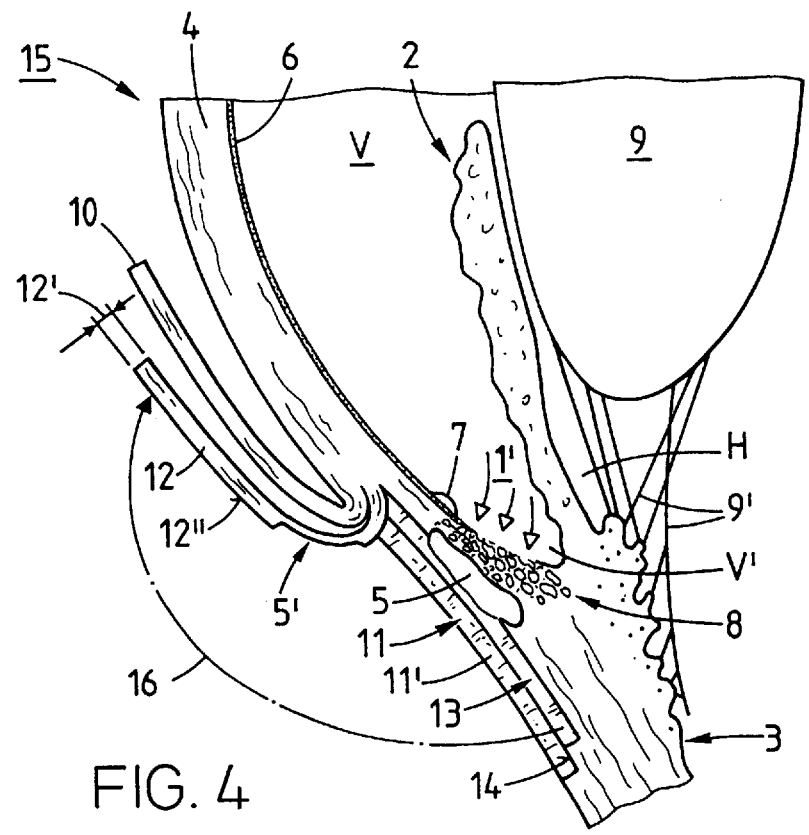
FIG. 4 is a schematic view of the portion of the eye of FIG. 3, illustrating both upwardly folded scleral flaps and taken along the line IV—IV in FIG. 3.

FIG. 4 shows the portion of eye 15, taken along the line IV—IV in FIG. 3, with the two scleral flaps 10, 12 folded upwards in the direction of arrow 16 and held in place by suitable means (not shown). The second incision results in a thickness 12' of the second scleral flap 12 that allows sufficient exposure and accessibility of the Schlemm's canal 5. This is essentially realized by selecting the depth of second incision in such a manner that a portion 5' of the Schlemm's canal 5 remains at the inside of the second scleral flap 12. As shown in FIG. 3, the attached portion 5' extends over the entire width of the second sclera flap 12 and has a substantially grooved configuration.

Figure 5:
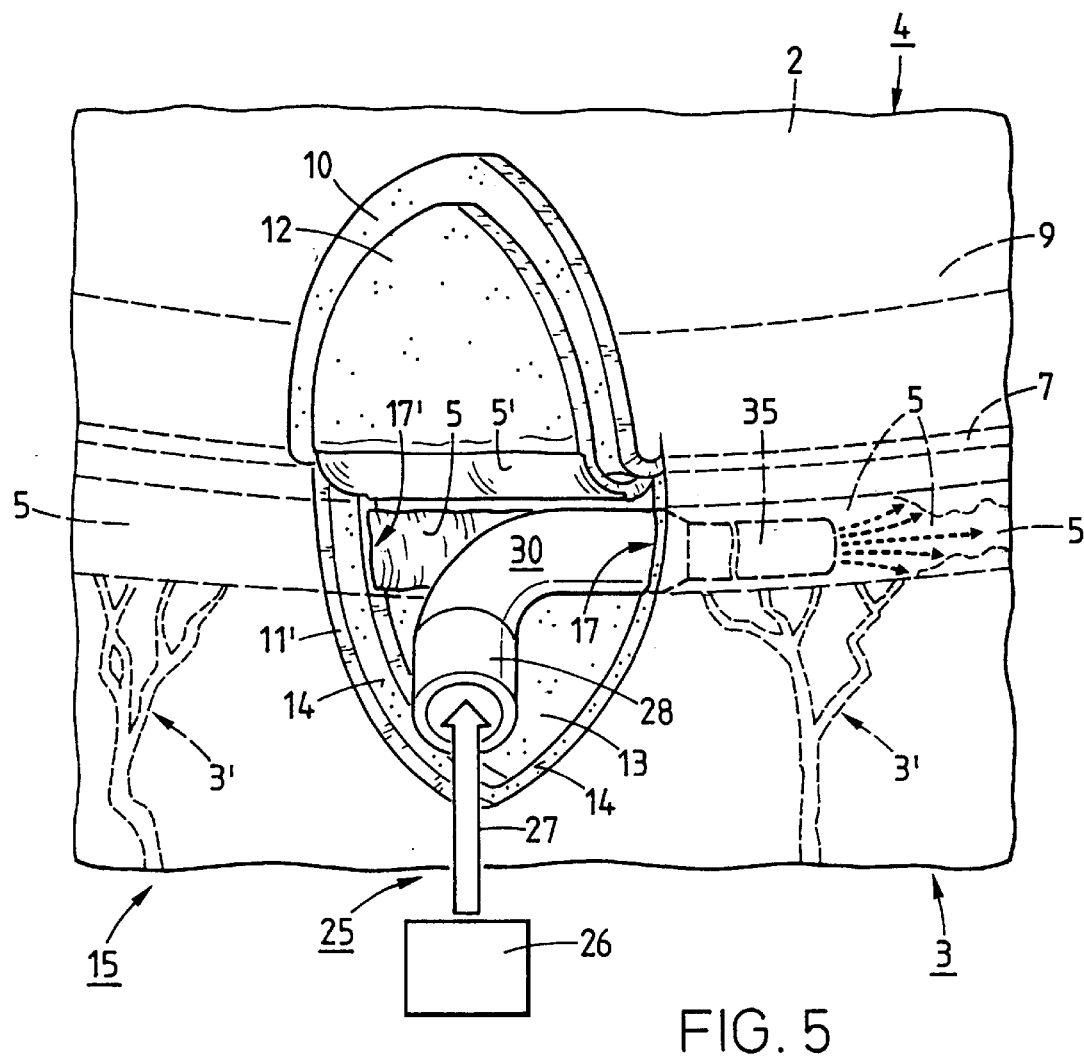
FIG. 5 is a schematic illustration of the portion of the eye of FIG. 3, depicting a first embodiment of a probe according to the present invention for insertion into the exposed canal of Schlemm, with the probe being attached to an arcuate adapter.

Turning now to FIG. 5, which is an enlarged illustration of the eye 15 of FIG. 3 and shows a portion of the sclera 3 and the two upwardly folded sclera flaps 10, 12 as well as the second recess 13 and the lateral support surface 14 of the sclera 3, to show a third phase of the novel and inventive process, in which a suitable medium, preferably a high viscosity sodium-hyaluronate solution (high viscosity hyaluronate) is injected into the two lateral openings 17 and 17' of the Schlemm's canal 5 by an injection unit, generally designated by reference numeral 25 to expand the lumen of the Schlemm's canal 5. The injection unit 25 includes a probe 35 which is attached to an arcuate adapter 30 and inserted into the exposed opening 17 of the Schlemm's canal 5 for injecting the high viscosity sodium hyaluronate solution. After expanding the lumen of the Schlemm's canal 5 at least along the entire length of the inserted probe 35, the injection unit 25 with the probe 35 is withdrawn from the opening 17 and turned for insertion in the opposite opening 17' of the Schlemm's canal for injection of the expanding medium and expansion of the lumen. The injection unit 25 is connected via a supply conduit 28 to pressure source 26 in the form of a single-chamber syringe or similar. The injected medium is forced into the lumen of Schlemm's canal in the direction of arrow 27, by means of the manually or electrically operated pressure source 26 for expansion of the lumen.

Figure 6:
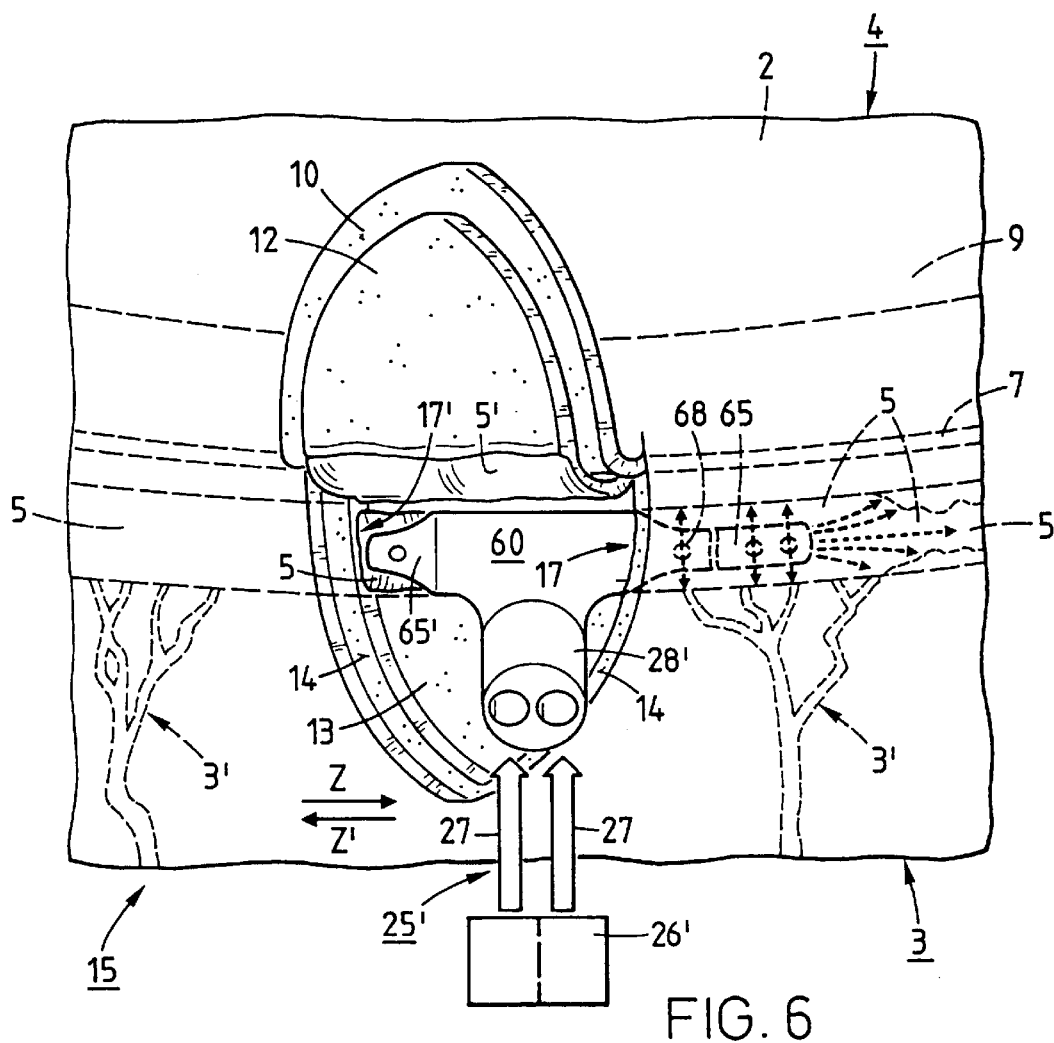
FIG. 6 is a schematic illustration of the portion of the eye of FIG. 3, depicting a second embodiment of a probe according to the present invention for insertion into the exposed canal of Schlemm, with the probe being attached to an adapter of T-shaped configuration.

FIG. 6 shows a variation of an injection unit, generally designated by reference numeral 25' and including an adapter 60 having a T-shaped configuration and provided with two probes 65, 65' in opposite disposition for injection of expanding medium through both openings 17, 17' of the Schlemm's canal. The adapter 60 is connected to a pressure source 26' via a supply conduit 28' which has two separate passageways in respective fluid communication with the probes 65, 65'. The injection unit 25' offers the option to insert the probe 65 in a first phase through movement in the direction of arrow Z into the opening 17 for injection of expanding medium. After expansion of the Schlemm's canal 5, the adapter 60 with the probe 65 is withdrawn from the Schlemm's canal 5 and slightly moved to the left in the direction of arrow Z' for inserting the probe 65' into the other opening 17' of the Schlemm's canal 5 for injection of expanding medium. This injection unit 25' is thus designed for successive injection of expanding medium through the openings 17 and 17'.

Persons skilled in the art will understand however that the T-shaped adapter 60 may certainly be designed in such a manner that simultaneous supply of expanding medium through the openings 17, 17' is also possible. In this case, the adapter 60 is handled such that initially the probe 65 is inserted through the opening 17 and then moved slightly to the left for insertion of the other probe 65' through the opposite opening 17'.

The injection unit 25' is connected via the supply conduit 28' to the manually or electrically actuated pressure source 26' which is formed as a dual chamber syringe. This allows operation of the injection unit 25' such that expanding medium can be injected sequentially or simultaneously via the probes 65, 65' into the lumen of the Schlemm's canal 5.

Figure 7:
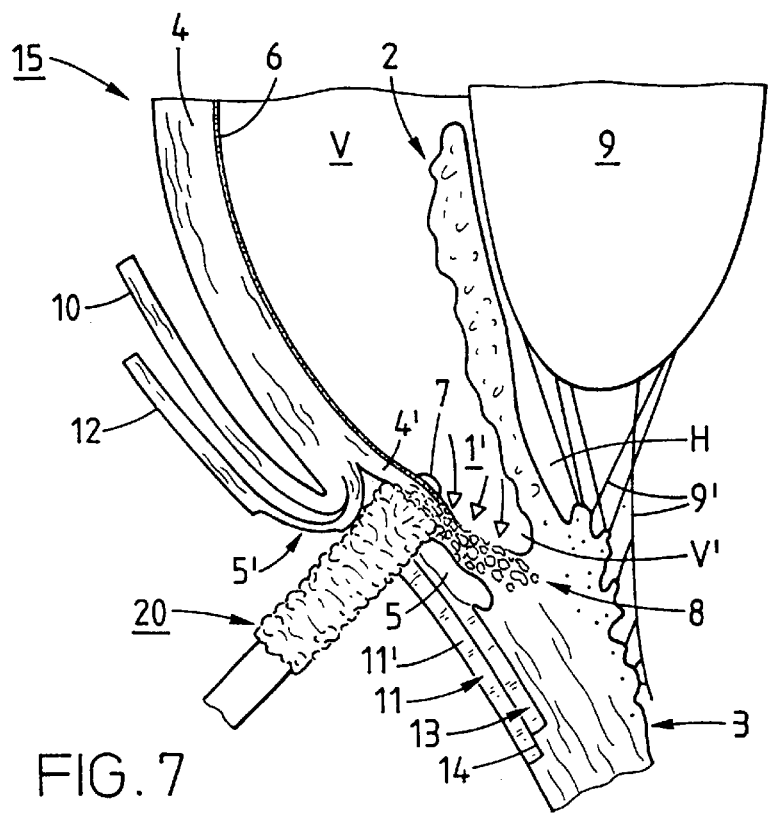
FIG. 7 is a schematic view of the portion of the eye of FIG. 4, illustrating the application of a swab for applying a small pressure force against the Schwalbe's Line in the area of the two upwardly folded scleral flaps.
Figure 8:
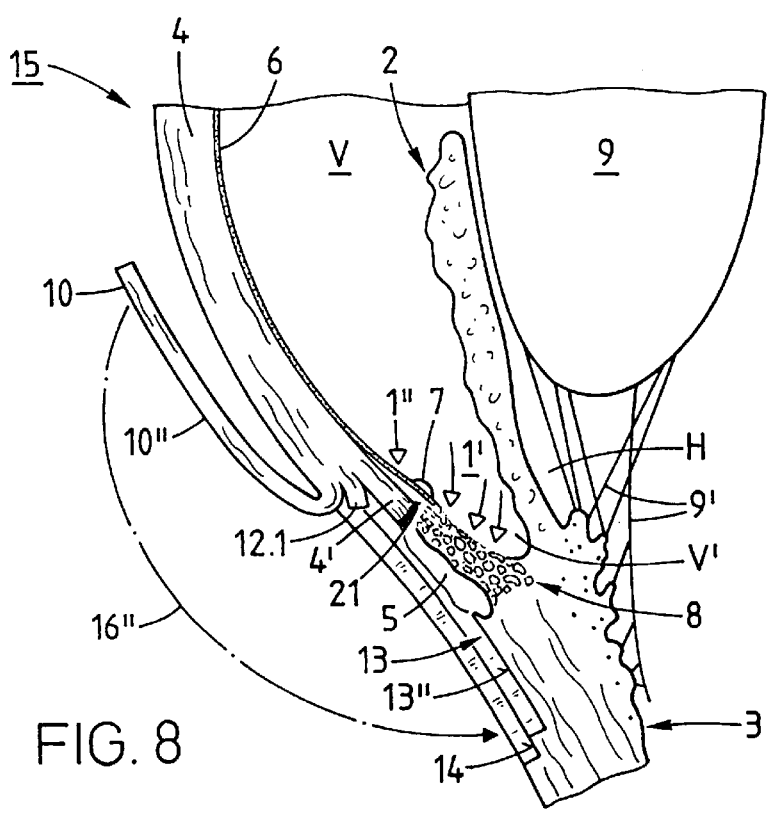
FIG. 8 is a schematic view of the portion of the eye of FIG. 7, illustrating a detachment of the Descemet's membrane from the cornea and severed second scleral flap.
Figure 9:
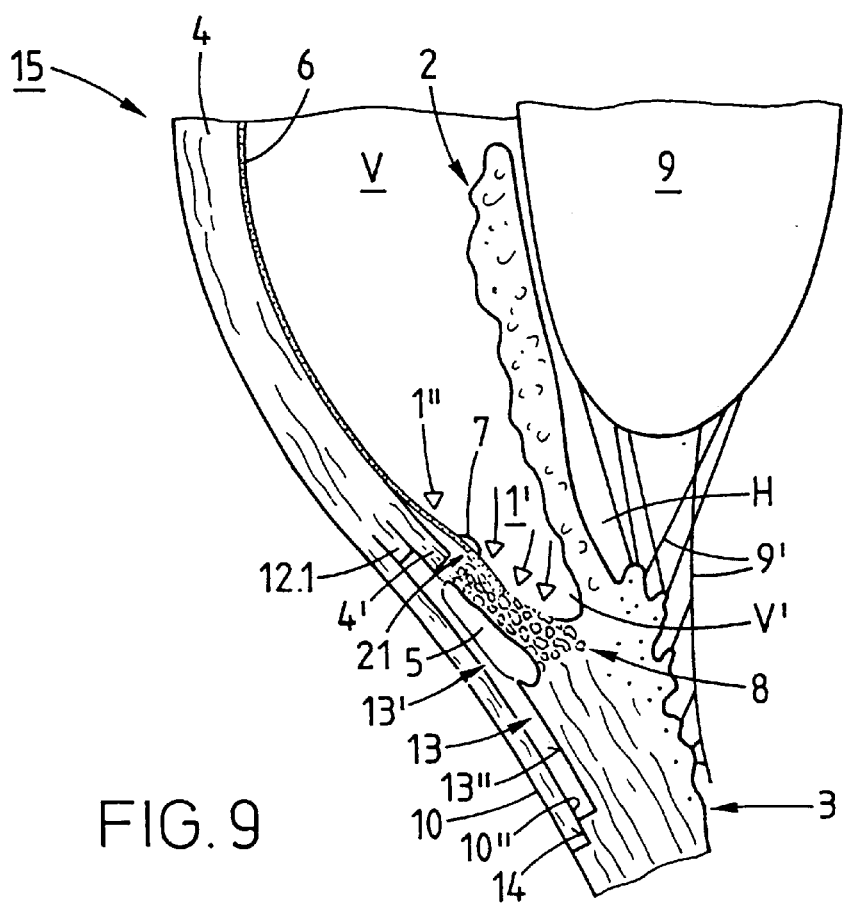
FIG. 9 is a schematic view of the portion of the eye of FIG. 8, illustrating the first scleral flap being folded downwards.

Turning now to FIG. 7, there is shown the next process step, after expansion of the Schlemm's canal 5 and withdrawal of the injection unit 25, 25', for detachment the Descemet's membrane 6 from the inner surface of the cornea in the area of the Schwalbe's line. The detachment of the Descemet's membrane 6 is realized by using a swab 20 for applying a slight force against the Schwalbe's line so as to create a passageway 21 between the cornea 4 and Descemet's membrane 6 as shown schematically enlarged in FIG. 8. The passageway 21 is approximately slit-shaped and extends in a manner not shown here across the entire width of the second recess 13. The passageway 21 provides a further connection between the anterior chamber V and the second recess 13 so that aqueous humor can drain apart from the natural outflow via the trabecular tissue 8 in the direction of arrow 1' also via the substantially transparent Descemet's membrane 6, which is partly permeable for aqueous humor in the direction of arrow 1", as indicated in FIGS. 8 and 9, and via the passageway 21 to the recess 13 which is fluidly connected with the Schlemm's canal 5. The second recess 13 which corresponds to the scleral flap 12 essentially forms a reservoir for aqueous humor for drainage into the Schlemm's canal 5.

In a next phase, the second scleral flap 12, save for a small remaining portion 12.1, is then severed with a suitable surgical instrument (not shown), as shown in FIG. 8. It will be appreciated by persons skilled in the art, that the separation of the second sclera flap 12 may be carried out also before detachment of the Descemet's membrane 6 with the swab 20 to form the passageway 21.

Next, while retaining the passageway 21, the first sclera flap 10 is folded downwards in the direction of arrow 16" (FIG.8) and placed upon the parabolic support surface 14, as shown in FIG. 9. Then, the first sclera flap 10 is sutured partially to the sclera 3. As the second sclera flap 12 has been separated, a subscleral space 13' is formed behind the first scleral flap 10 and filled by means of a syringe (not shown) with high viscosity medium, such as sodium hyaluronate, before completely rejoining the first scleral flap 10. This prevents an inside surface 10" of the first scleral flap 10 to come into contact with the inside surface 13" of the recess 13, as shown in FIG. 9.

Referring now to FIG. 10, there is shown a detailed illustration of the arcuate adapter 30 with attached probe 35. The adapter 30 has a first leg 36 terminating in an inlet port 31, and a second leg 36' which defines an interior space 31' in fluid communication with the inlet port 31 and bounded by a wall 32. Formed integrally with the second leg 36' of the adapter 30 is the tube-like probe 35 which has interiorly a continuous axial bore 33 forming an outlet channel and fluidly communicating with the interior space 31' of the arcuate-shaped adapter 30. For ease of insertion into the Schlemm's canal, the probe 35 has an adapter-distal end 34 of rounded configuration. At its other end, the probe 35 is connected to adapter 30 via a transition piece 37 which flares outwardly toward the second leg 36' of the adapter 30. The conical or circular arc shaped transition piece 37 ensures a sealing contact when the probe 35 is inserted through the openings 17, 17' of the Schlemm's canal 5, so as to substantially prevent leakage of injected fluid in case of back-up in the lumen of the Schlemm's canal 5.

As shown in FIG. 10, the probe 35 is formed as an elongate, flexible tube which is made of transparent, flexible plastic material, e. g. polymide or polytetrafluoro-ethylene, or may be made of flexible metal tube or a flexible metal, e.g. stainless steel or a nickel-titanium alloy to thereby impart the probe 35 with sufficient flexibility that permits free movement with respect to the longitudinal axis X, as indicated in dash-dot lines, while preventing a breakage when the probe 35 is of a longer configuration. Suitably, the probe 35 further includes a plurality of apertures 38 which are spaced from one another in axial direction and fluidly connected with the bore 33 for additionally providing an exit for injection of medium into the Schlemm's canal 5. Although not shown, it is certainly possible to so configure the probe 35 as to flare outwardly between the end 34 and the transition piece 37. In view of its flexibility, the tubular probe 35 can conform its orientation and disposition to the respective inner configuration of the Schlemm's canal 5 when being inserted into the Schlemm's canal 5.

FIG. 10A shows another embodiment of a combined adapter-probe arrangement which includes an adapter 30' for attachment of a probe 35'. The second leg 36' of the adapter 30' is formed with a terminal recess 36" for receiving the confronting end of the probe 35' which is secured therein e.g. by gluing. The tube-like probe 35' is connected with the interior space 31' via an axial bore 33' which forms an outlet port and a plurality of exit apertures 38' spaced from one another in axial direction and fluidly connected with the bore 33' for injection of medium into the Schlemm's canal. Suitably, the probe 35' has an end face 34' of back-slanted configuration. The adapter 30' terminates in a circular arc shaped end face 37' which has a greater outer diameter that the outer diameter of the probe 35' to thereby form a shoulder. This ensures a substantial sealing contact upon the opening 17, 17' when the probe 35' is inserted into the Schlemm's canal 5, thereby preventing leakage of injected medium upon a possible backup in the lumen of the Schlemm's canal 5.

FIG. 10B shows a another variation of a combined adapter-probe arrangement which is illustrated here only by way of a tube-like probe 35" which has interiorly an axial bore 33" and a plurality of side-by-side exit apertures 38" for injection of expanding medium into the Schlemm's canal. At its adapter-distal end face 34", the probe 35" is formed with a circular bead 39.

It will be understood that attachment of the probe 35' to the adapter 30' according to FIG. 10A and attachment of the probe 35" to the adapter 30" according to FIG. 10B is realized in a same manner as previously described in connection with the probe 35 in FIG. 10, and connected at the arcuate adapter 30, are made from a flexible plastic tube or from a flexible metal tube having limited flexibility, for example, stainless steel or a nickel/titanium alloy.

FIG. 11 shows a partially sectional front view of another embodiment of a combined adapter-probe arrangement, with an arcuate adapter 40 having an inlet port 41. The adapter 40 has a first leg 46 and a second leg 46' and is essentially configured in correspondence to the adapter 30 of FIG. 10. Attached to the second leg 46' is a relatively short probe 45 which defines a longitudinal axis X and has formed interiorly therein an axial bore 43 to form an outlet channel in fluid communication with an interior space 41' of the adapter 40 in the form of an outlet port. The probe 45 is further provided with a plurality of axially spaced apart apertures 48 which are in fluid connection with the bore 43. For ease of insertion into the Schlemm's canal 5, the probe 45 has an end face 44 of rounded configuration.

At its other end, the probe 45 is formed to the second leg 46' via an outwardly flared transition piece 47. This conical or circular arc-shaped transition piece 47 ensures a sealing contact when inserting the probe 45 into the opening 17, 17' of the Schlemm's canal 5 so that escape of injected medium due to a backup in the lumen of Schlemm's canal 5 is substantially prevented. It is certainly also possible to configure the probe 45 such as to flare outwardly from the end face 44 in the direction of the transition piece 47.

The interior space 41' in the second leg 46' of the adapter 40 has a funnel-shaped inner wall 42 which, starting from the inner diameter of the interior space 41' tapers in the direction of the bore 43. The thus nozzle-shaped tapered inner wall 42 effects a compressed and pressure-accelerated discharge of medium injected into the lumen of Schlemm's canal 5. FIG. 11A shows a cross-sectional view, taken along the line XI—XI, of the adapter 40 with the first leg 46 and the probe 45 with the circular arc shaped bore 43.

Although not shown in the drawings, it will be appreciated by persons skilled in the art that the probe 45 may also be designed in correspondence with the probe 35' of FIG. 10A, or the probe 35" of FIG. 10B.

FIG. 10C shows the probe 35.1 with a distal end and a proximal end, which is connected to the adapter and wherein the probe flares outwardly from the distal end to the proximal end.

FIG. 11B shows a first variation of the probe 45 in the form of a tube having a substantially elliptical shape and formed interiorly with a bore 43' as outlet channel of elliptic configuration. In FIG. 11C, the probe 45 is in a disposition rotated by a right angle α with respect to the longitudinal axis X for ease of handling and better insertion into the Schlemm's canal 5, whereas in FIG. 11D, the probe 45 is arranged at an obtuse angle α' to the second leg 46'.

FIG. 12 shows still another embodiment of a combined adapter-probe arrangement with an arcuate adapter 50 having an inlet port 51. The adapter 50 includes a first leg 56 and a second leg 56' and is essentially designed in correspondence to adapter 30 of FIG. 10, or FIG. 10A, or FIG. 10B, or in correspondence to adapter 40 of FIG. 11, or FIG. 11A to FIG. 11D. Attached to the second leg 56' is an elongate probe 55 having an elliptical or circular ring shaped cross section. Departing from the embodiment according to FIG. 10 and FIG. 11, the probe 55 is provided at its outer circumference with axial grooves 53 to form an outlet channel. Each of the grooves 53 is in fluid connection with an interior space 51' of the second leg 56', with the interior space 51' being bounded by a wall 52 of the second leg 56'. Suitably, the probe 55 has an end face 54 of rounded configuration.

At its other end, the probe 55 is formed to the second leg 56' of the adapter 50 via an outwardly flared transition piece 57. The conical or circular arc shaped transition piece 57 provides a sealing contact when the probe 55 is inserted into the opening 17, 17' of the Schlemm's canal 5 so that leakage of injected medium, due to possible back-up in the lumen of Schlemm's canal 5, is substantially prevented.

The probe 55 may also be made, like the probe 35, as a flexible plastic tube having limited flexibility so as to be freely movable with respect to the longitudinal axis X.

FIG. 12A shows a sectional view of the adapter-probe arrangement, taken along the line XII—XII in FIG. 12, and depicts the circular configuration of the probe 55 which is formed with, for example, four grooves 53 evenly spaced about its circumference and fluidly connected with the interior space 51' of the adapter 50. FIG. 12B shows a variation of the probe 55 which has an elliptic cross section and is formed with four grooves 53 evenly spaced about its circumference and fluidly connected with the interior space 51' of the adapter 50.

The adapters 30, 40, or 50 as depicted in FIGS. 10 to 12 and the respectively attached probes 35, 45, or 55 are so configured that medium is injected into the lumen of the surgically exposed Schlemm's canal 5 successively through either in the one or the other opposite opening.

Turning now to FIG. 13, there is shown another embodiment of a combined adapter-probe arrangement including an adapter 60 for use with the injection unit 25' schematically shown in FIG. 6. The approximately T-shaped adapter 60 has an upper portion 66' for connection of two probes 65 and 65' arranged in opposite disposition and having interiorly an axial bore 63. Formed integrally with the upper portion 66' is a leg 66 which extends perpendicular to the leg 66' and has two separate entry ports 61 and 61' in fluid communication with the bores 63 of probes 65 and 65'. It will be appreciated that the probes 65 may have different lengths, as schematically shown in FIG. 6. Probe 65 may be designed, analogous to probe 35, as a flexible tube which is freely movable in its disposition and orientation with respect to the longitudinal axis X to conform to the inner configuration of the lumen of the Schlemm's canal 5 when inserted therein. Both probes 65 and 65' may also have a cross section in correspondence to the probes of FIG. 11A or FIG. 11B or according to the probes shown in FIGS. 12A and 12B.

Each probe 65 has an end face 64 of rounded configuration. Its other end is connected to the upper portion 66' of the adapter 60 via an outwardly flared transition piece 67. The conical or circular arc shaped transition piece 67 ensures a sealing contact when the probe 65 is inserted in the Schlemm's canal 5 so that leakage of the medium due to a possible back-up in the lumen of Schlemm's canal 5 is substantially prevented.

While the invention has been illustrated and described as embodied in a method of and device for improving the flow of aqueous humor within the eye, it is not intended to be limited to the details shown since various modifications and structural changes may be made without departing in any way from the spirit of the present invention.

What is claimed as new and desired to be protected by Letters Patent is set forth in the appended claims:

What is claimed is:

1. A device for improving the draining of aqueous humor in a surgically exposed Schlemm's canal in an eye of a living being, comprising a injection unit and an adapter which has a substantially circular arcuate configuration with at least one probe disposed with a proximal end to the adapter, wherein the probe is provided with at least one outlet channel along a longitudinal axis and in fluid communication with an interior space of the adapter and the injection unit, said probe insertable into at least one location of the circular Schlemm's canal exposed by surgical sclera incision, for injecting a viscous medium to thereby generate a localized pressure buildup, wherein said probe includes a transition piece integrally formed with the adapter and having a conical configuration for sealing contact with a lumen of the Schlemm's canal, said probe is defined by a diameter and an axial length, with the length being sized at least twice the diameter and wherein the probe has a distal end configured for free motion with respect to the disposition and orientation of the longitudinal axis.

2. The device of claim 1, wherein the probe is made of flexible plastic material.

3. The device of claim 1, wherein the probe is made of transparent plastic.

4. The device of claim 1, wherein the probe is a flexible tube from metal.

5. The device of claim 4, wherein the metal is a nickel titanium alloy.

6. The device of claim 1, wherein the probe has a distal end and a proximal end, said probe flaring outwardly from the distal end in the direction of the proximal end.

7. The device of claim 1, wherein the probe has a proximal end and a distal end, and is disposed at the adapter, said probe is configured for free motion at least at the distal end with respect to the longitudinal axis and freely movable with respect to disposition and orientation.

8. The device of claim 1, wherein the probe is configured for free motion along an entire axial extension of the probe and is provided with a plurality of apertures which are spaced from one another in axial direction and fluidly connected with the outlet port.

9. The device of claim 1, wherein the probe has a proximal end and a distal end and includes a transition piece integrally formed with the adapter, said transition piece having a conical configuration or a circular arc shaped configuration for sealing contact with the Schlemm's canal.

10. A device for improving the draining of aqueous humor in a surgically exposed Schlemm's canal in an eye of a living being, comprising a injection unit and an adapter with at least one probe disposed with a proximal end to the adapter, wherein the probe is provided with at least one outlet channel along a longitudinal axis and in fluid communication with an interior space of the adapter and the injection unit, said probe insertable into at least one location of the circular Schlemm's canal exposed by surgical sclera incision, for injecting a viscous medium to thereby generate a localized pressure buildup, wherein said probe includes a transition piece integrally formed with the adapter and having a conical configuration for sealing contact with a lumen of the Schlemm's canal, said probe is defined by a diameter and an axial length, with the length being sized at least twice the diameter and wherein the probe has a distal end configured for free motion with respect to the disposition and orientation of the longitudinal axis, wherein the probe is configured as a elongated tube with a cross section selected from one of a circular ring shape or an elliptical shape, said tube having an inner axial bore which forms an outlet port and is in fluid communication with an interior space of the adapter, which has a substantially circular arcuate configuration.

11. The device of claim 10, wherein the probe is provided with more than one axial bore forming outlet ports.

12. A device for improving the draining of aqueous humor in a surgically exposed Schlemm's canal in an eye of a living being, comprising a injection unit and an adapter with at least one probe disposed with a proximal end to the adapter, wherein the probe is provided with at least one outlet channel along a longitudinal axis and in fluid communication with an interior space of the adapter and the injection unit, said probe insertable into at least one location of the circular Schlemm's canal exposed by surgical sclera incision, for injecting a viscous medium to thereby generate a localized pressure buildup, wherein said probe includes a transition piece integrally formed with the adapter and having a conical configuration for sealing contact with a lumen of the Schlemm's canal, said probe is defined by a diameter and an axial length, with the length being sized at least twice the diameter and wherein the probe has a distal end configured for free motion with respect to the disposition and orientation of the longitudinal axis, wherein the probe is configured as a elongated tube with a cross section selected from one of a circular ring shape or an elliptical shape, said tube having an inner axial bore which forms an outlet port and is in fluid communication with an interior space of the adapter, which has a substantially circular arcuate configuration, wherein the interior space of the adapter is dimensioned with a diameter greater than that of the outlet port for accelerated injection of the viscous medium into the Schlemm's canal.

13. A device for improving the draining of aqueous humor in a surgically exposed Schlemm's canal in an eye of a living being, comprising a injection unit and an adapter with at least one probe disposed with a proximal end to the adapter, wherein the probe is provided with at least one outlet channel along a longitudinal axis and in fluid communication with an interior space of the adapter and the injection unit, said probe insertable into at least one location of the circular Schlemm's canal exposed by surgical sclera incision, for injecting a viscous medium to thereby generate a localized pressure buildup, wherein said probe includes a transition piece integrally formed with the adapter and having a conical configuration or an arcuate configuration for sealing contact with a lumen of the Schlemm's canal, said probe is defined by a diameter and an axial length, with the length being sized at least twice the diameter and wherein the probe has a distal end configured for free motion with respect to the disposition and orientation of the longitudinal axis, wherein the probe has a distal end and a proximal end, said probe flaring outwardly from the distal end in the direction of the proximal end.

* * * * *